(12) United States Patent
Caron et al.

(10) Patent No.: US 7,858,074 B2
(45) Date of Patent: Dec. 28, 2010

(54) RHEOLOGICAL ADDITIVE IN THE FORM OF A PREACTIVATED PASTE

(75) Inventors: Sébastien Caron, Montreuil sur Thérain (FR); Susan Rimmer, Chantilly (FR); Yohann Trang, Lyons (FR); Elizabeth Pires, Creil (FR); Joël Roussel, Lacroix Saint Ouen (FR)

(73) Assignee: Cray Valley S.A., Courbevoie (FR)

( * ) Notice: Subject to any disclaimer, the term of this patent is extended or adjusted under 35 U.S.C. 154(b) by 303 days.

(21) Appl. No.: 11/957,805

(22) Filed: Dec. 17, 2007

(65) Prior Publication Data

US 2008/0153924 A1  Jun. 26, 2008

Related U.S. Application Data

(60) Provisional application No. 60/913,875, filed on Apr. 25, 2007.

(30) Foreign Application Priority Data

Dec. 21, 2006  (EP) .................................. 06292039

(51) Int. Cl.
    *C08K 5/20* (2006.01)
(52) U.S. Cl. ................... 424/63; 106/243; 106/31.13; 106/504; 106/38.7; 514/772; 524/186
(58) Field of Classification Search ........................ None
    See application file for complete search history.

(56) References Cited

U.S. PATENT DOCUMENTS

| 4,088,601 | A | * | 5/1978 | Shane et al. ................. 516/121 |
| 5,180,802 | A | * | 1/1993 | Hartman et al. ............. 528/335 |
| 5,349,011 | A | * | 9/1994 | Reichert et al. ............. 524/602 |
| 5,902,841 | A | * | 5/1999 | Jaeger et al. ................ 523/161 |
| 6,448,366 | B1 | * | 9/2002 | Santhanam et al. ......... 528/288 |
| 2005/0256262 | A1 | * | 11/2005 | Hill et al. .................... 524/702 |

FOREIGN PATENT DOCUMENTS

| EP | 467533 A1 | 1/1992 |
| JP | 63015876 | 1/1988 |
| JP | 2002146336 | 5/2002 |
| JP | 2004107543 | 4/2004 |

OTHER PUBLICATIONS

Jayflex™ DIUP from ExxonMobil Chemical.*
Rahman et al., "The plasticizer market: an assessment of traditional plasticizers and research trends to meet new challenges," Prog. Polym. Sci. 29 (2004) 1223-1248.*
Cray Valley Coating Resins Technical Data Sheet: Crayvallac MT, Jul. 2006.*
Cray Valley Technical Paper: Methoxysilane Sealants: One-Component Moisture Curing Methoxysilane Sealants, Mar. 2001.*
Cray Valley "One-Component Moisture CuringMethoxysilane Sealants" Technical Data Information Sheet (Mar. 2001) [Cray Valley.*
ExxonMobil Chemical Product Sheet.*
Rahman et al ("The plasticizermarket: an assessment of traditional plasticizers and research trends to meet new challenges," Progress in Polymer Science (2004) 1123-1248.*

* cited by examiner

*Primary Examiner*—Yvonne L Eyler
*Assistant Examiner*—Suzanne Ziska
(74) *Attorney, Agent, or Firm*—Whyte Hirschboeck Dudek SC

(57) ABSTRACT

The invention relates to a rheological additive in the form of a preactivated paste, comprising: A) at least one fatty acid diamide introduced in powder form, it being possible for the powder optionally to comprise, in addition to the diamide, hydrogenated castor oil, B) at least one organic plasticizer, the plasticizer being liquid at room temperature. A specific process for the preparation of this rheological additive, a composition comprising the additive, a process for the preparation of the composition and specific uses, in particular specific coatings obtained from the additive, are also disclosed.

17 Claims, 4 Drawing Sheets

RHEOLOGICAL ADDITIVE IN THE FORM OF A PREACTIVATED PASTE

CROSS REFERENCE TO RELATED APPLICATIONS

This application claims priority to pending European Patent Application No. 06 292 039.2, filed Dec. 21, 2006, and pending U.S. Provisional Patent Application No. 60/913,875 filed Apr. 25, 2007, both of which are hereby incorporated by reference in their entirety.

BACKGROUND

The present invention relates to rheological additives in the form of a preactivated pastes, to a specific process for the preparation of these additives, to specific compositions comprising the said additives, and also to a specific process for the preparation of said compositions, to specific uses and to the specific coatings obtained from said additives. These specific additives allow the modification of the viscosity of sealant compositions, glue compositions, adhesive compositions, coating compositions, such as paints, varnishes, gel coats or inks, or molding compositions.

The state of the art reveals sealant compositions, adhesive compositions or coating compositions based on polyurethane comprising an additive of non-reactive polyamide type for adjusting the viscosity of said compositions. Specifically, EP 467 533 describes a polyamide obtained from at least one polycarboxylic acid chosen from sebacic acid, azelaic acid, dodecanedioic acid and fatty acid dimers or trimers with at least one component containing an —$NH_2$ or —NH group chosen from primary or secondary monoamines natural or synthetic, saturated or unsaturated, either ethylenically or acetylenically unsaturated. The obtained polyamide rheological additive can be prepared as a powder, or in combination with a solvent or a plasticizer, forming a liquid or a paste, said polyamide being previously diluted therein.

JP 2004107543 discloses a thixotropic additive in the paste form which is free from granular particles, said paste being the product of the reaction between a diamide component and an epoxy resin added at the end of the synthesis step, said diamide component being chemically modified in order to be able to react with the epoxy resin.

Furthermore, JP 2002146336 discloses the preparation of a rheological additive in the paste form obtained from a blend of fatty acid diamides, dispersed in an alcohol-based solvent, of a compound of cycloaliphatic type and of an ester. The obtained dispersion is then subjected to a thermal treatment. The final paste does not comprise any plasticizer; it is subsequently used as thixotropic agent in unsaturated polyester resins.

JP 63-15876 discloses a mixture of hydrogenated castor oil fatty acid and of saturated $C_{14}$-$C_{18}$ fatty acid with ethylene diamine or 1,4-diaminobutane, the mixture forming a thixotropic agent which can be used in one-component polyurethane sealant compositions. However, said thixotropic agent is not provided in the form of a preactivated paste which can be used without any preliminary activation.

Other rheological additives can be used to increase the viscosity of solvent-based or solvent-free sealants or adhesive systems. Among them we may cite polyamide powders, powders based on hydrogenated castor oil derivatives, fumed silicas, precipitated or ground calcium carbonates. The fumed silicas and calcium carbonates are of mineral (inorganic) nature and require a very high speed dispersion of the mixture. However, these inorganic fillers exhibit problems of stability and of sedimentation over time, with resulting negative effects on the mechanical properties of the final system. Another particular disadvantage of polyamide powders and of powders formed of derivatives of hydrogenated castor oil, is the need for the end-user (formulator) to activate the system (powder) during the production of the final application composition. This activation requires high speed shearing, and heating to temperatures ranging up to near 120° C. depending on the products, and also a necessary minimum dwell time (duration), depending on (determined by) the temperature conditions and on the system (polarity), in order to develop optimum final rheological properties. These additives confer, on the composition into which they are incorporated, a thixotropic behavior characterized by a significant shear thinning, that is to say a reduction in the viscosity when the shearing increases and then a time-dependent recovery of the viscosity (equivalent to a hysteresis effect). Additives of this type provide the final composition with excellent applicative properties which are characterized by high viscosity at rest, good stability of this viscosity on storage, good resistance to sedimentation, ease of application and of extrusion and good sag resistance once applied. Despite the fact that additives of this type provide the final composition with good properties, they exhibit, as a main disadvantage, the fact that they do need an activation step, which is sometimes difficult to control or to reproduce by the end-user, and costly in terms of both time and of energy.

The technical problem of the invention, with respect to the cited prior state of the art, thus consists to develop an improved product (additive) exhibiting comparable properties to those shown by polyamide powders and hydrogenated castor oil derivatives, but without requiring a phase of activation by the end-user, said product consequently being much easier and much faster to use by the end-user, with further specific advantages linked to the resolution of this general problem. The term "in the preactivated paste form" should be considered as meaning that the additive is ready-for-use by the end-user (formulator of sealants, of glues, of adhesives or of coatings, such as paints or varnishes or gel coats or inks, or of molding compositions), by simple mixing into the final application formulation, without needing any specific in situ activation in the said formulation (requiring specific conditions of temperature, of shearing and of duration to be respected).

More particularly, the advantages linked to the resolution of the general technical problem with respect to the prior art are as follows:

low Volatile Organic Compounds (VOC) emissions and reduced risk of inflammation or of explosion, absence of handling pulverulent (micronized) powders by the end-user, thus preventing dust formation in the atmosphere and on the production site of the final compositions and consequently the need for ventilation due to the risk of dust inhalation, possibility of handling in the absence of any solvent in the final formulation, it being possible for the additive to be used both in solvent-based application compositions and in solvent-free compositions, flexibility of use and of handling, the preactivated paste being easy to disperse in the composition, either at the same time as the fillers at the beginning of production, or at the end of processing, while conserving rheological properties at least equivalent to those obtained from powders of polyamide or diamide type or castor oils according to the prior art, finally and in particular, no need for the activation stage, the processing of the additive according to the invention requiring neither heating nor high shearing nor an activation time, which allows a saving:

- in terms of production time, since there is no heating stage and since the cooling stage is shortened, even avoided, during the preparation of the final composition,
- in energy, due to the absence of the heating and cooling stages,
- in productivity for the end-user,
- in reproducibility and reliability of the final end-use performances.

BRIEF DESCRIPTION OF THE DRAWINGS

The change in the elastic and viscous moduli of the reference example (non-preactivated composition) and of the example of the invention (preactivated paste) in DIUP as a function of the maturing time is presented in FIG. 1.

The change in the elastic and viscous moduli of the reference example (non-preactivated composition) and of the example of the invention (preactivated paste) in PPG 2000 as a function of the maturing time is presented in FIG. 2.

Figure 3:
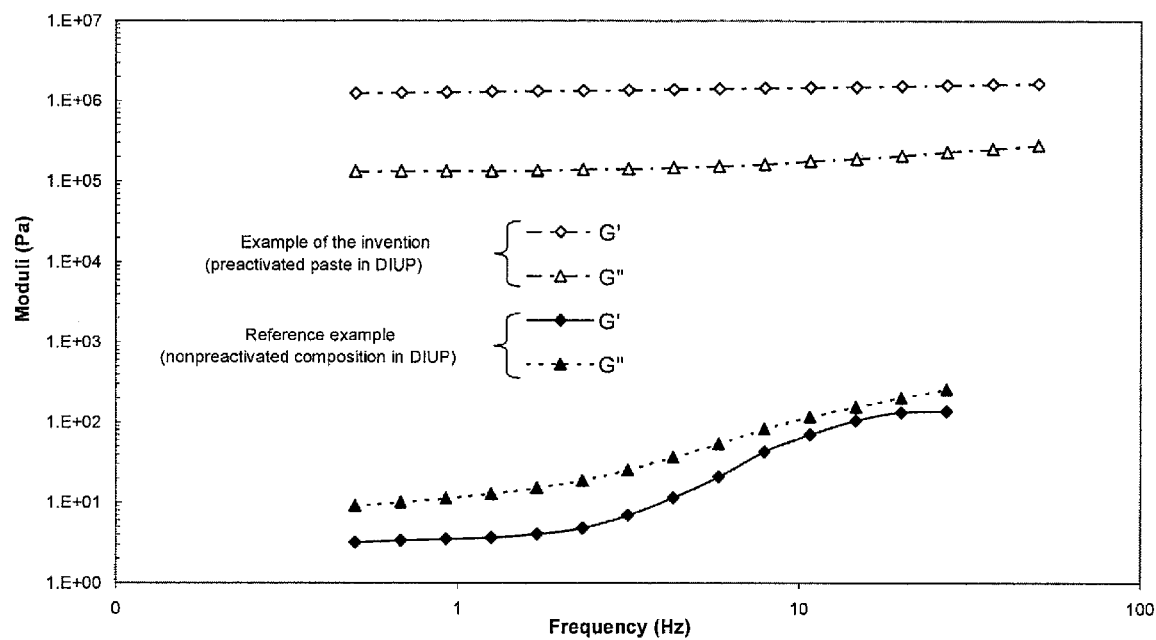

The change in the dynamic elastic and viscous moduli of the reference example (non-preactivated composition) and of the example of the invention (preactivated paste) in DIUP as a function of the frequency is presented in FIG. 3.

Figure 4:
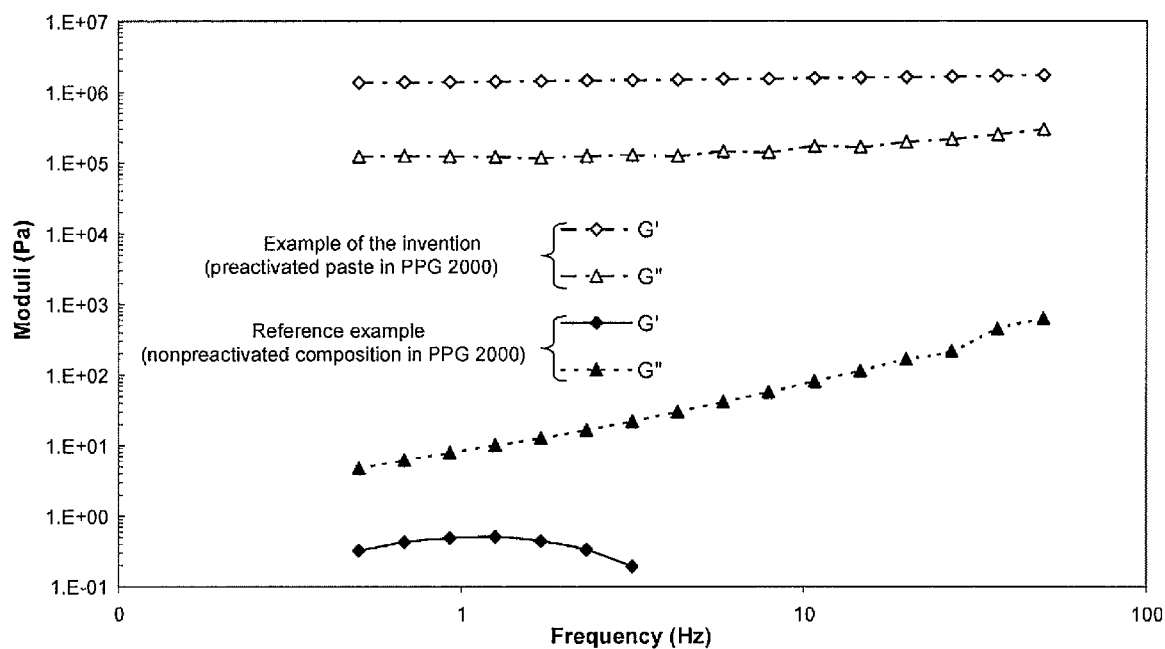

The change in the dynamic elastic and viscous moduli of the reference example (non-preactivated composition) and of the example of the invention (preactivated paste) in PPG 2000 as a function of the frequency is presented in FIG. 4.

Thus, the first subject matter of the invention is a rheological additive in the form of the preactivated paste, comprising:

A) at least one fatty acid diamide introduced in the powder form, it being possible for said powder optionally to comprise, in addition to said diamide, hydrogenated castor oil, B) at least one organic plasticizer, said plasticizer being liquid at room temperature.

The second subject matter of the invention is a process for the preparation of such rheological additives by dispersion and activation under controlled heating.

The invention also relates to a composition of organic binder or of pigment concentrate or of fillers comprising a rheological additive according to the present invention and to the process for the preparation of such a composition.

Another subject matter of the invention is the use of the rheological additive or of the composition according to the invention in coating applications for paints, varnishes, inks, gel coats or plastisols based on PVC or for applications of sealants, glues, adhesives, sealers or of molding compositions or also for cosmetic applications.

Finally, a last subject matter of the invention relates to finished articles, such as coatings, seals, molded composites or components, or cosmetics, obtained from the additive or from the composition according to the invention.

The first subject matter of the invention is thus a rheological additive in the form of a preactivated paste, comprising:

A) at least one fatty acid diamide introduced in the powder form, it being possible for said powder optionally to comprise, in addition to said diamide, hydrogenated castor oil, B) at least one organic plasticizer, said plasticizer being liquid at room temperature.

Said rheological additive in the form of a preactivated paste preferably exhibits a dynamic elastic modulus G', measured on said mixture A)+B), at a temperature of 23° C. and under a frequency of 1 Hz, higher than or equal to $10^4$ Pa, preferably higher than or equal to $8 \times 10^4$ Pa and more preferably still higher than or equal to $5 \times 10^5$ Pa. This characteristic does significantly show the effective activation of the preactivated additive.

Preferably, said plasticizer is a polar organic plasticizer bearing at least one polar group, preferably an ether group and/or an ester group and/or an epoxy group.

Said plasticizer can first bear at least one ether group, and in this case it can be chosen from polyethers, such as homopolymers and/or copolymers of ethylene oxide and/or of propylene oxide and/or a blend of said polyethers (homopolymers and/or copolymers) and/or their derivatives, these derivatives comprising, inter alia, said polyethers which are blocked at the chain end by a $C_1$ (methoxy) to $C_4$ (butoxy) alkoxy group or by a $C_2$ (acetate) to $C_4$ (butyrate) ester group, said polyethers having a weight-average molecular weight Mw ranging from 150 to 6000 and preferably from 1000 to 3000. The term "copolymer" is to be interpreted as comprising both random and block copolymers.

Said plasticizer may further bear at least one ester group and it may be chosen from monoesters and/or polyesters (multi- or poly-functional esters) obtained from $C_4$ to $C_{21}$ alcohols, which alcohols are optionally alkoxylated, for example with 1 to 10 alkoxy units chosen from oxyethylene (OE) and/or oxypropylene (OP) units, and from mono- or polyacids with a functionality ranging from 1 to 4 selected from:

organic acids chosen from aromatic acids having a chain length (without —$CO_2H$ functional group) ranging from $C_6$ to $C_{10}$ and/or aliphatic acids having a chain length (without considering the —$CO_2H$ functional group) ranging from $C_4$ to $C_{18}$, or inorganic acids.

The esters of aromatic acids may be chosen from phthalic esters (phthalates) and trimellitic or trimellitate esters (benzene 1,2,4-tricarboxylate) and their trimesitate or trimesate isomers (benzene 1,3,5-tricarboxylate). The esters of aliphatic acids can be chosen from adipic esters (adipates), citric esters (citrates), sebacic esters (sebacates) and azelaic esters (azelates). The esters of inorganic acids can be chosen from sulfonic esters (sulfonates), in particular $C_{10}$ to $C_{21}$ alkyl sulfonates, sulfuric esters (sulfates), sulfinic esters (sulfinates), phosphoric esters (phosphates), phosphonic esters (phosphonates) and phosphinic esters (phosphinates).

Finally, said plasticizer may also bear at least one epoxy group and may be chosen from epoxidized oils based on fatty acid, the chain length of which can range from $C_{16}$ to $C_{18}$, such as epoxidized soybean oil.

Preferably, in said rheological additive, there is an absence of any other compound selected from alcohols with a molecular weight Mw<150, such as methanol, ethanol, propanol, butanol or benzyl alcohol, or selected from polar aprotic solvents, such as N-methylpyrrolidone, N-ethylpyrrolidone, N-butylpyrrolidone, acetonitrile, N,N-dimethylformamide, N,N-dimethylacetamide, dimethyl sulfoxide, N,N,N',N'-tetramethylurea, hexamethylphosphoramide, hexamethylphosphorous triamide or propylene carbonate.

Among the preferred plasticizers can be cited those comprising at least one $C_6$ to $C_{10}$ aromatic acid ester group, in particular plasticizers selected from mono- and/or dialkyl phthalates and more preferably still from dialkyl phthalates, with it being possible for said alkyls to be identical or different and chosen from $C_7$ to $C_{18}$ and preferably $C_{10}$ to $C_{12}$ alkyls.

The most preferred in this family of plasticizers (dialkyl phthalates) is di-iso-undecyl phthalate. The most preferred in the family of polyethers are the polyethers which are homopolymers of propylene oxide (polypropylene glycols) with a weight-average molecular weight Mw ranging from 1000 to 3000, more particularly polypropylene glycol (PPG) with an Mw equal to 2000, and/or their derivatives chosen from monoesters, preferably $C_2$ to $C_4$ monoesters, or $C_1$ to $C_4$ monoethers, such as monomethoxy or monoethoxy derivatives.

Said plasticizer can have a boiling point higher than 200° C. and preferably higher than 250° C. (at atmospheric pressure). It must be liquid at room temperature in order for said diamide to be dispersible in said plasticizer.

The rheological additive according to the invention preferably exhibits a maximum penetration value or consistency, measured according to standard ASTM D 217, of less than 15 mm, more preferably of less than 10 mm and more preferably still of less than 5 mm.

Said fatty acid diamide introduced in the powder form has a particle size of less than 100 μm and preferably of less than 50 μm and more preferably at least 90% of said diamide has a particle size of less than 20 μm and preferably of less than 15 μm.

The weight ratio of the fatty acid diamide can vary from 10 to 40% and preferably from 15 to 30%, with respect to the mixture A)+B).

A fatty acid diamide suitable for the invention, can be obtained by polycondensation between at least one $C_2$ to $C_{12}$ primary diamine and at least one monocarboxylic acid with a chain length of $C_3$ to $C_{22}$, it being possible for the reaction product optionally to be diluted in hydrogenated castor oil and in this case to a weight ratio varying from 10 to 100% by weight, with respect to the diamide+hydrogenated castor oil total, preferably to a weight ratio varying from 20 to 100% by weight. The hydrogenated castor oil can be used to adjust the affinity of the final mixture (diamide+hydrogenated castor oil) with respect to the composition of the final application formulation.

In the case where the diamide is diluted in hydrogenated castor oil, the addition takes place at a temperature of between 140 and 220° C. At the end of the addition, a solid mass is obtained and is milled (micronized).

According to a preferred embodiment of the invention, the rheological additive according to the invention is obtainable by a specific process, such as described below.

The specific process for the preparation of said rheological additive, which is the second subject matter of the invention, comprises the following steps i) progressive dispersing of said diamide in the powder form in the plasticizer until a homogeneous dispersion is obtained, at room temperature controlled by virtue of regulation of the temperature, the diamide and said plasticizer being as defined above, ii) maintaining the homogeneous dispersion obtained during stage i) at least one isotherm with a corresponding temperature ranging from 50 to 120° C. and preferably from 60 to 100° C., for a period of time of 1 to 100 hours, preferably of 6 to 80 hours and more preferably still of 15 to 40 hours.

The choice of the temperature and the duration of step ii) depends on the polarity of the plasticizer and on its chemical affinity with said fatty acid diamide.

The homogeneity of the dispersion is characterized by an absence of granular particles (bits) when the film of said dispersion is applied between two glass sheets (glass sheets test). In order to obtain this homogeneity, said diamide is dispersed in said plasticizer at a shear rate preferably of between 2 and 6 m·s$^{-1}$ for a preparation on the laboratory scale with a volume not exceeding 1 liter.

The end of step ii), also known as "activation or maturation step", is characterized by a maximum penetration value or consistency of the formed paste of less than 15 mm, preferably of less than 10 mm and more preferably still of less than 5 mm, measured according to standard ASTM D 217. This maximum penetration value is to be associated with a reference method for the preparation of said preactivated paste, which corresponds to a preparation on the laboratory scale with a volume not exceeding 1 liter, the sample being thus perfectly homogeneous. The method for the preparation of said preactivated paste is described below in the examples according to the invention.

The third subject matter of the invention relates to a composition formed of organic binder or of pigment concentrate or of fillers comprising at least one rheological additive as defined according to the invention or obtained according to the process as defined according to the invention, it being possible for said binder composition to be a coating composition for the protection and/or decoration and/or surface treatment of various substrates, said coating composition may be selected from paints, varnishes, pigmented or clear gel coats, inks or plastisols based on PVC, or it being also possible for the said binder composition to be a sealant, glue, adhesive or sealers composition, or also a molding composition for molded composites or for molded pieces (parts or articles), SMC or BMC or laminates type, boat hull or composite panel types, or pieces molded by casting, with application of the composition with a brush or with a roller, or by spraying with a spray gun, or finally a cosmetic composition.

Said rheological additive according to the invention as described above can be present in said composition at a weight ratio varying from 1 to 40%, preferably from 15 to 30% and more preferably still from 10 to 20%, with respect to the total weight of said composition, and said diamide can be present as dry active material, at a weight ratio varying from 0.1 to 16%, preferably from 0.2 to 8% and more preferably still from 1 to 6%, with respect to the total weight of said composition.

The composition according to the invention can comprise other components, such as, for example, fillers, plasticizers, wetting agents or also pigments.

According to a more particular embodiment, the organic binder composition according to the invention is crosslinkable, either thermally or by irradiation under radiation, such as UV radiation (in the presence of at least one photoinitiator) and/or EB radiation (electron beam, without initiator), including self-crosslinkable at room temperature, or it may be non crosslinkable. The organic binder composition can be a one-component crosslinkable composition (just one reactive component) or a two-component crosslinkable composition (binder based on two components which react with one another by mixing during use).

Said organic binder can be selected from at least one epoxy/amine (crosslinkable two-component) reactive system, an unsaturated polyester, a vinyl ester, an epoxidized resin, a reactive silicone resin, an alkyd grafted by a polyester or a polyamide or an alkyd modified by diurea/diurethane or an ungrafted alkyd, a polyurethane or a silicone, a crosslinkable two-component polyurethane, a polysiloxane, a polysulfide polymer, a reactive acrylic polymer, a (meth)acrylate multifunctional oligomer or acrylated acrylic oligomer or allylic multifunctional oligomer, a butyl rubber, polychloroprene or SBR type elastomer, or a silylated prepolymer or polymer, preferably a silylated polyether or a silylated polyurethane, or a silylated polyether-urethane with an —OH or —CO$_2$H functional group.

In a more specific case, said organic binder can be selected from the following crosslinkable two-component reactive systems epoxy/amine or epoxy/polyamide systems comprising at least one epoxy resin comprising at least two epoxy groups and at least one amino or polyamide compound comprising at least two amine groups, polyurethane systems comprising at least one polyisocyanate and at least one polyol, polyol/melamine systems, and polyester systems based on at least one epoxy or on one polyol which reacts with at least one acid or corresponding anhydride.

According to other specific cases, said organic binder can be a crosslinkable two-component polyurethane system or a crosslinkable two-component polyester system from an epoxy/carboxylic acid or anhydride reaction system, or from a polyol/carboxylic acid or anhydride system, or from a polyol/melamine reaction system in which the polyol is a hydroxylated acrylic resin, or a polyester or a polyether polyol.

According to an alternative form, the organic binder composition according to the invention is a sealant, glue, adhesive or sealer composition which is self-crosslinkable and based on polyether-silane or on polyurethane-silane.

More particularly, the organic binder composition according to the invention can be a one-component sealant composition based on a silylated prepolymer or polymer, and preferably a silylated polyether or a silylated polyurethane (silylated polyether-urethane), such as Kaneka MS Polymer™ and Kaneka Silyl™. MS Polymers™ can be used in:

the construction and building industry for expansion joints, the fitting of glazing, carpentry joints, masonry joints, prefabricated materials (sandwich panels for refrigerated lorries, for example) or parquet flooring, the naval industry, the motor vehicle industry (industrial bodywork, windscreen profile rubbers), mass market (do it yourself: DIY market) for sealants and adhesives, with and without solvent, civil engineering.

Other components can be added to or substituted in one-component sealant compositions based on silylated prepolymer or polymer, such as other types of binders, colored pigments, various plasticizers, fillers of precipitated or ground calcium carbonate type, glyceride derivatives, silicas, such as fumed silicas, other additives, such as UV-A absorbers (UV antioxidants), such as 2,4-di(tert-butyl)-6-(5-chlorobenzotriazol-2-yl)phenol (Tinuvin® 327 from Ciba), light stabilizers based on sterically hindered amines, such as HALS (hindered amine light stabilizers), for example bis(2,2,6,6-tetramethyl-4-piperidyl) sebacate (Tinuvin® 770 from Ciba), waxes and other types of catalysts, such as tin salts.

The invention also comprises a process for the preparation of said composition according to the invention, said process comprising the following stages i) addition of said additive according to the invention to said composition, ii) homogenization of the mixture with a agitator and/or planetary mixer and/or high speed disperser, without having any need, at this stage, to apply any activation treatment.

Said process for the preparation of said organic binder composition according to the invention can also comprise a preliminary stage of preparation of said additive according to the following steps i) preparation of an additive according to the invention according to the process for the preparation of said additive of the invention as defined above, ii) addition of said additive obtained according to step i) to said composition as defined above, iii) homogenization of the mixture in an agitator and/or planetary mixer and/or high speed disperser, without having any need, at this stage, to apply any activation treatment.

The term "high speed" means tangential speeds ranging from 2 to 15 m·s$^{-1}$.

Another subject matter according to the invention relates to the use of at least one rheological additive or of a composition according to the present invention, without the need for in situ activation, by simple addition to and homogenization in the final formulation. More particularly, said rheological additive and said composition can be used in coating applications, such as coatings for paints, varnishes, inks, pigment-comprising or pigment-free gel coats or plastisols based on PVC, or in sealants, glues, adhesives or sealers applications, molding composition applications for composites, molded compounds or SMC/BMC laminates, or in cosmetic applications, such as nail varnishes.

Finally, the last subject matter of the invention relates to the finished items, such as coatings, obtained from the use of at least one rheological additive or from the use of a composition according to the present invention or by the use of the respective preparation processes, said coatings being selected from paints, or varnishes, or inks, or pigmented or clear (non-pigmented) gel coats, or plastisols based on PVC, or sealants, or glues, or adhesives, or sealers (seals), or composites, or molded components, or SMC/BMC laminates resulting from molding compositions, or also cosmetic products, such as nail varnishes.

By way of illustration of the invention, the following examples demonstrate, without any limitation, the performance of the rheological additive according to the present invention.

I—STARTING MATERIALS USED

TABLE 1

|  | Role | Commercial reference | Supplier |
| --- | --- | --- | --- |
| Silylated polyether | Binder | MS Polymer ™ S203H | Kaneka |
| Silylated polyether | Binder | MS Polymer ™ S303H | Kaneka |
| Di-iso-undecyl phthalate (DIUP) | Plasticizer | Javflex ® DIUP | Exxon Mobil |
| Polyamide | Rheological additive | Crayvallac ® SL | Cray Valley |
| Calcium carbonate | Filler | Carbital ® C110S | Imerys |
| Titanium dioxide | Pigment | RL 90 | Millenium |
| 2,4-Di(tert-butyl)-6-(5-chlorobenzotriazol-2-yl)phenol | UV stabilizer | Tinuvin ® 327 | Ciba |
| Bis(2,2,6,6-tetramethyl-4-piperidyl) sebacate | Light stabilizer | Tinuvin ® 770 | Ciba |
| Silane | Dehydrating agent | Dynasilan ® VTMO | Degussa Sivento |
| Silane | Adhesion promoter | Dynasilan ® DAMO | Degussa Sivento |
| Tin salt | Catalyst | Metatyn ® KAT 740 | Acima |

II—PREPARATION AND CHARACTERIZATION OF THE RHEOLOGICAL ADDITIVES FATTY ACID DIAMIDE AND PREACTIVATED PASTE

Preparation of the Fatty Acid Diamide:

450 g of 12-hydroxystearic acid and 430 g of capric acid are heated to 80° C. 120 g of ethylenediamine are subsequently charged. The amine reacts immediately with the acids to form the corresponding salts. This results in an exothermic reaction which causes the temperature in the reactor to rise from 80 to 130° C. The reactor is subsequently rapidly heated until the batch temperature reaches 200° C. The reactor is subsequently maintained at this temperature until the acid and amine numbers are less than 6 mg KOH/g. The contents of the reactor are subsequently discharged, cooled and then finely milled (micronised).

Preparation of the Pastes:

REFERENCE EXAMPLES

Compositions which are not Preactivated a) Plasticizer: DIUP 100 g of premilled fatty acid diamide and 300 g of di-iso-undecyl phthalate (DIUP) are dispersed for 1 hour using a Dispermat® CV dissolver equipped with a disk with a diameter of 4 cm, at a speed of 2000 revolutions/min (or rpm), at a temperature not exceeding 20° C., by regulation of the temperature by circulation of cold water.

b) Plasticizer: PPG 2000

100 g of premilled fatty acid diamide and 300 g of polypropylene glycol with a weight of 2000 (PPG 2000) are dispersed for 1 hour using a Dispermat® CV dissolver equipped with a disk with a diameter of 4 cm, at a speed of 2000 revolutions/min (or rpm), at a temperature not exceeding 20° C., by regulation of the temperature by circulation of cold water.

EXAMPLES OF THE INVENTION

Preactivated Pastes a) Plasticizer: DIUP

The same procedure is followed as for the reference example, with an additional stage of maturing consisting in introducing the non-preactivated composition for 24 hours into an oven heated beforehand to 80° C.

b) Plasticizer: PPG 2000

The same procedure is followed as for the reference example, with an additional stage of maturing consisting in introducing the non-preactivated composition for 24 hours into an oven heated beforehand to 80° C.

Rheological Characterization of the Pastes:

The rheology of the pastes is controlled at 23° C. using a MCR301 (Anton Paar) controlled-stress rheometer, equipped with a geometry of plate/sanded plate with a diameter of 25 mm and with an air gap of 0.5 mm.

1) Monitoring of the Activation

The activation of the pastes was evaluated by monitoring, in dynamic mode, the elastic modulus (G') and the viscous modulus (G") of the pastes as a function of the maturing time. The moduli were measured on samples at different maturing times (the measurements were carried out 10 minutes after removing from the oven, the time for the temperature of the sample to fall to 23° C.).

The stress τ is chosen so as to lie within the linear region (at low strain). The frequency used is 1 Hz.

Figure 1:
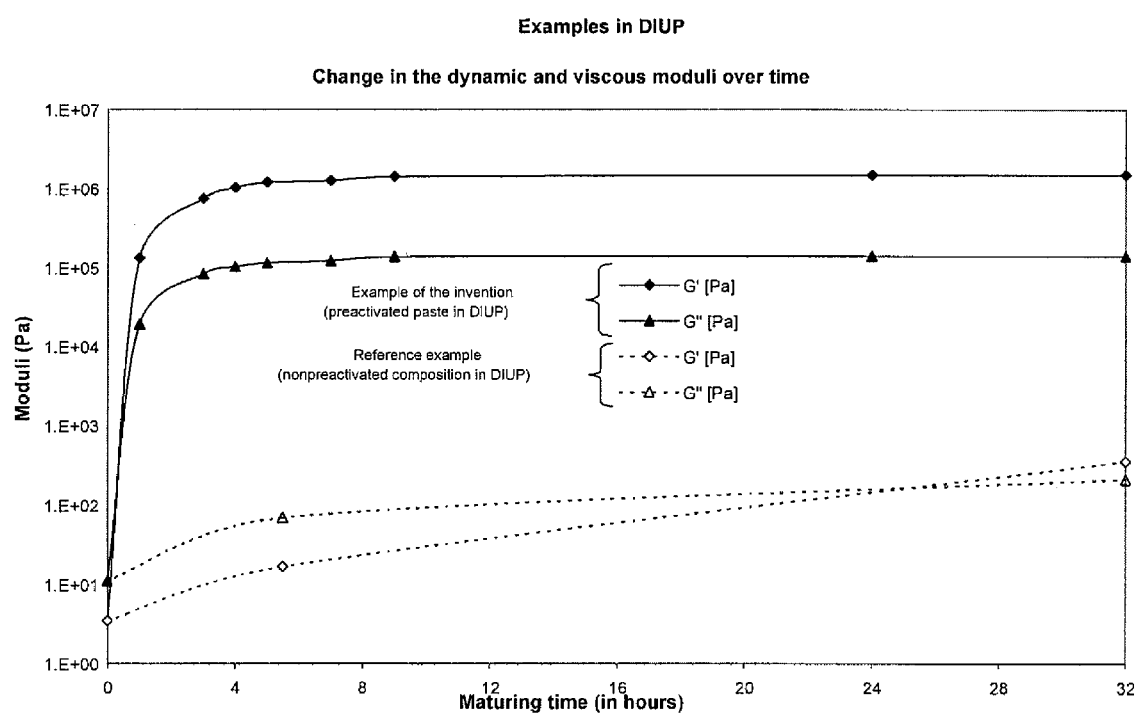
Figure 2:
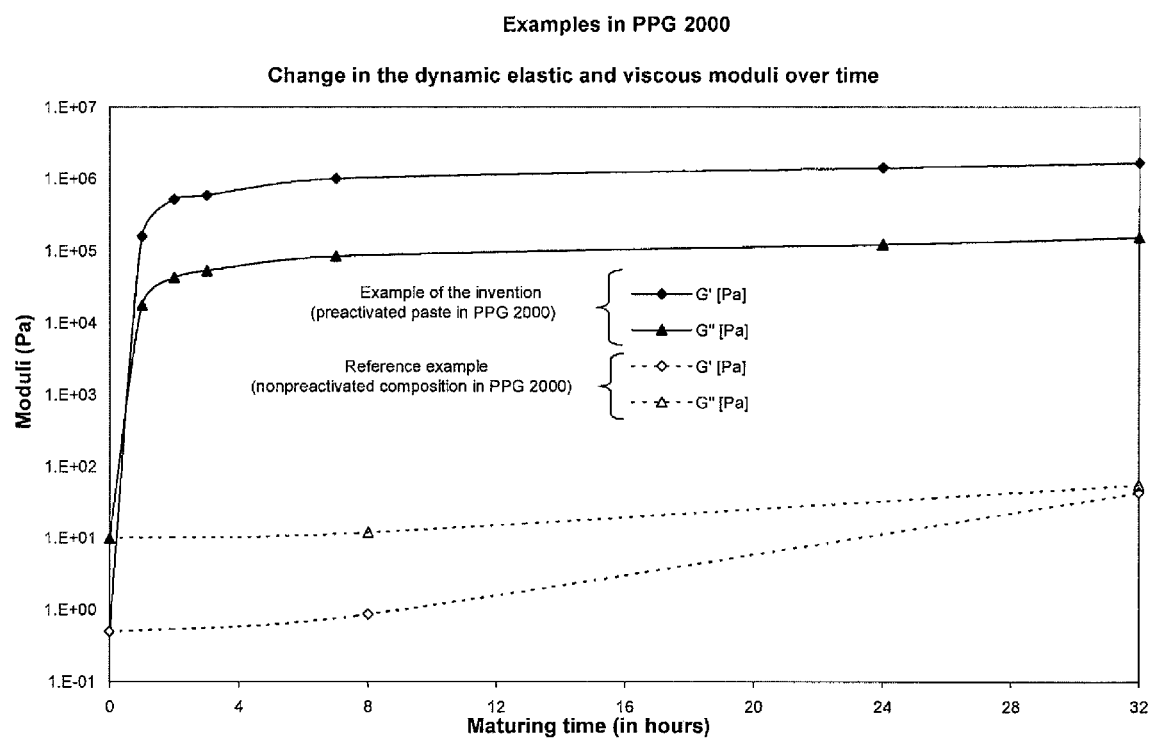

The corresponding curves are presented in FIGS. 1 and 2.

2) Frequency Mechanical Spectra

The frequency mechanical spectra of the pastes were recorded at 23° C.

The change in the elastic moduli (G') and viscous moduli (G") as a function of the frequency was monitored in dynamic mode.

The corresponding curves are presented in FIGS. 3 and 4.

III—PREPARATION AND USE OF THE RHEOLOGICAL ADDITIVES FOR THE PREPARATION OF SEALANTS

Preparation of the Preactivated Pastes:

a) Plasticizer: DIUP 250 g of the premilled fatty acid diamide and 750 g of di-iso-undecyl phthalate (DIUP) are charged to a 1 liter vessel (height 13 cm, diameter 11 cm) at room temperature. The two products are mixed at 1500 revolutions/min for 15 min, using a Dispermat® CV dissolver equipped with a disk with a diameter of 4 cm, at a temperature not exceeding 20° C., by regulation of the temperature by circulating with cold water. The vessel is subsequently carefully closed and introduced for 24 hours into an oven preheated beforehand to 70° C.

The final product is a soft white paste characterized by a dry active matter content of 25% and a resistance to penetration, measured according to standard ASTM D 217, of 2.00 mm.

b) Plasticizer: PPG 2000

250 g of the premilled fatty acid diamide and 750 g of polypropylene glycol with a weight of 2000 (PPG 2000) are charged to a 1 liter vessel (height: 13 cm, diameter: 11 cm) at room temperature. The two products are mixed at 1500 revolutions/min for 15 min, using a Dispermat® CV dissolver equipped with a disk with a diameter of 4 cm, at a temperature not exceeding 20° C., by regulation of the temperature by circulating with cold water. The vessel is subsequently carefully closed and introduced for 24 hours into an oven preheated beforehand to 70° C.

The final product is a soft white paste characterized by a dry active matter content of 25% and a resistance to penetration, measured according to standard ASTM D 217, of 3.11 mm.

The rheological additive in the form of a preactivated paste is used in the preparation of sealants of MS Polymer™ type.

The rheological additive is stored in the absence of water and of moisture in order to prevent any initiation of polymerization by crosslinking. The crosslinking reaction (self-crosslinking) takes place at the time of use, in the presence of room moisture, at a relative humidity (RH)>50%.

Manufacture of the Sealant:

The sealants are manufactured in the laboratory with a device of Molteni Labmax disperser D2 (series 2000) type. This equipment makes it possible to reproduce industrial conditions but on a small scale (pilot scale). It is equipped with a planetary disperser with a diameter of 65 mm, with a scraper and with a vacuum pump which prevents moisture from entering during the manufacturing. This device makes it possible to manufacture 1500 g of product, which is equivalent to three cartridges. The cartridges used are Fischbach E310 HPDE, 310 ml, cartridges—accessories KO1-DO1A0.

The MS polymers and the DIUP plasticizer are mixed at 1000 revolutions/min, at a tangential speed of 3.5 m·s$^{-1}$, for 5 minutes. The rheological additive is subsequently added and dispersed at 2600 revolutions/min (8.8 m·s$^{1}$), the mixture being maintained at a temperature of 30° C. by circulation of water.

The light and UV stabilizers, the titanium dioxide and also the calcium carbonate, having been pre-dried at 90° C. for 12 hours, are incorporated and then dispersed under vacuum at 2600 revolutions/min. The fillers are completely dispersed after approximately one hour.

IV—CHARACTERIZATION METHODS

The rheological behavior of the compositions comprising at least one additive according to the present invention was characterized according to the following tests 1) Extrudability or Grammage 1-1) Principle This method is specific to the determination of the extrudability of a one-component sealant from the cartridge in which it has been packaged, the one-component sealant being extruded under compressed air pressure.

The extrudability is expressed by a weight extruded over a defined time (g·min$^{-1}$).

1-2) Equipment

The equipment used is as follows:
an air gun for the application of the sealant on a building site,
an air compressor with a valve and a pressure gauge for maintaining the compressed air supply at 250±10 KPa (i.e., 2.5 bar±0.1 bar),
a plastic cylinder with a volume of 500 ml,
a stopwatch calibrated in seconds,
an extrusion nozzle with an orifice with a diameter of 5±0.3 mm,
a precision balance for weighing the sample during the extrusion.

1-3) Conditioning of the Products

The products to be tested are conditioned for 24 hours in a climate-controlled laboratory at 23° C. and 50% RH before the beginning of the test.

1-4) Preparation of the Products

The end of the threaded bush of a cartridge (Fischbach E310 HPDE, 310 ml, cartridge—accessories KO1-DO1A0) has to be cut in order to form the widest possible orifice, with a diameter of at least 6 mm. The extrusion nozzle is then screwed onto the cartridge.

1-5) Rheological Characterization Procedure

The test is carried out at the temperature of the climate-controlled laboratory (23° C. and 50% RH). Three tests are carried out on the same cartridge.

The cartridge, prepared as above, is placed in the air gun and then the compressed air feed is increased up to 250 KPa.

The sealant is extruded from the cartridge into the nozzle, in order to fill it completely and thus to release any air possibly enclosed in the packaging. The gun is subsequently positioned vertically above the cylinder, itself placed on the balance.

The extrusion and the stopwatch are started simultaneously.

Approximately 100 g of sealant are extruded.

The extrusion and the stopwatch are stopped, again simultaneously.

The test is repeated twice. For each test, the flow rate of the extrusion is calculated, in g·min$^{-1}$, from the weight of sealant extruded as a function of the extrusion time.

2) Viscosity

The evaluation of the Brookfield® viscosity is carried out at 23° C. and 50% RH, with a No. 95 T-shaped spindle and at three different speeds 1, 5 and 10 revolutions/min (or rpm), on a Brookfield® viscometer with Hélipath™ system according to standard EN ISO 2555. The Brookfield® viscosity is expressed in mPa·s. The result is the expression of a mean of six values.

3) Thixotropic Index

The thixotropic index (V1/V10) equal to the ratio of the Brookfield® viscosity obtained at 1 revolution/min to the Brookfield® viscosity obtained at 10 revolutions/min, is calculated.

This relative value indicative of the thixotropic behavior is commonly used in the industrial field.

4) Consistency

The consistency of the pastes is measured by virtue of a texturing device, according to standard ASTM D 217. The standard refers to a standardized manual measuring device and has been reproduced by a TA-XT2i texture analyzer manufactured by Thermorheo (supplier Swantech). The principle of the standard has been automated on the TA-XT2i of Stable Micro Systems.

4-1) Principle

A suitable cone as described in standard ASTM D 217 is used with a given force in order to provide a value for penetration into the paste. This measurement of indentation is expressed in millimeters (mm).

The resistance to penetration increases with the consistency and the penetration value decreases with this consistency.

4-2) Equipment

The equipment used is as follows
an automatic texture analyzer: TA-XT2i,
a cone, the applied force of which is equivalent to its weight of 47.5 g, with a needle forming an angle of 30°.

4-3) Conditioning of the Products

The products to be tested have to be conditioned in a climate-controlled laboratory, under temperature and humidity conditions of 23±1° C. and 50±5% RH, for a period of time of 24 hours at least before the beginning of the test.

4-4) Preparation of the Products

The products are packaged after the synthesis in 1 liter vessels (height 13 cm, diameter: 11 cm).

The texture measurement is carried out after the maturing stage and before the samples are used.

4-5) Procedure

The test is carried out at the temperature of the climate-controlled laboratory. Three tests are carried out on each container.

The sample is placed under the cone and the point of the needle is placed at the surface of the paste.

The program on the TA-XT2i is subsequently started and the penetration is triggered.

The value of the displacement of the needle into the paste is subsequently recorded.

The results are expressed in millimeters (mm).

V—EXAMPLES

1) Examples of Sealants Formulated with the Additive in the Form of a Non-Preactivated Composition (Reference Example) and with the Additive in the Form of a Preactivated Paste (Example of the Invention) in DIUP The reference additive (non-preactivated composition) and the additive of the invention (preactivated paste), in DIUP, were evaluated in the following sealant formulation:

TABLE 2

| Starting material references | Nature | Example with the non-preactivated composition (reference) | Example with the preactivated paste (invention) |
|---|---|---|---|
| MS Polymer™ S203H | Silylated polyether | 14.89 | 14.89 |
| MS Polymer™ S303H | Silylated polyether | 9.92 | 9.92 |
| Jayflex® DIUP | Di-iso-undecyl phthalate (DIUP) | 17.37 | 17.37 |
| Rheological additive (100% active) | — | 3.72 | 3.72 |
| Carbital® C110S | Calcium carbonate | 49.63 | 49.63 |
| RL 90 | Titanium dioxide | 2.48 | 2.48 |
| Tinuvin® 327 | 2,4-di(tert-butyl)-6-(5-chlorobenzotriazol-2-yl)phenol | 0.25 | 0.25 |
| Tinuvin® 770 | Bis(2,2,6,6-tetramethyl-4-piperidyl) sebacate | 0.25 | 0.25 |
| Dynasilan® VTMO | Silane | 0.74 | 0.74 |
| Dynasilan® DAMO | Silane | 0.50 | 0.50 |
| Metatyn® KAT 740 | Tin salt | 0.25 | 0.25 |
| Total | | 100.00 | 100.00 |

Results

TABLE 3

| Example | Plasticizer | Extrudability (g/min) | Viscosities (mPa · s) | | | Thixotropic index |
|---|---|---|---|---|---|---|
| | | | 1 rpm | 5 rpm | 10 rpm | |
| Reference ex. (with non-preactivated composition) | DIUP | 1473 | 340 000 | 152 000 | 104 000 | 3.3 |
| Ex. of the invention (with preactivated paste) | DIUP | 688 | 2 040 000 | 734 000 | 441 000 | 4.6 |

2) Examples of Sealants with Different Additives

Four different sealant formulations were produced:
Example 1: additive-free sealant,
Example 2: sealant with a Crayvallac® SL powder additive,
Example 3: sealant with a preactivated paste in DIUP,
Example 4: sealant with a preactivated paste in PPG 2000.
The 4 examples were produced according to the formulations indicated in table 4:

TABLE 4

| Starting material references | Nature | Ex. 1 | Ex. 2 | Ex. 3 | Ex. 4 |
|---|---|---|---|---|---|
| MS Polymer™ S203H | Silylated polyether | 18 | 18 | 18 | 18 |
| MS Polymer™ S303H | Silylated polyether | 12 | 12 | 12 | 12 |
| Jayflex® DIUP | Di-iso-undecyl phthalate (DIUP) | 15 | 15 | 3.6 | 3.6 |
| Crayvallac® SL | Polyamide | 0 | 3.8 | 15.2* | 15.2* |
| Carbital® C110S | Calcium carbonate | 46.1 | 46.1 | 46.1 | 46.1 |
| RL 90 | Titanium dioxide | 2.0 | 2.0 | 2.0 | 2.0 |
| Tinuvin® 327 | 2,4-Di(tert-butyl)-6-(5-chlorobenzotriazol-2-yl)phenol | 0.3 | 0.3 | 0.3 | 0.3 |
| Tinuvin® 770 | Bis(2,2,6,6-tetramethyl-4-piperidyl) sebacate | 0.3 | 0.3 | 0.3 | 0.3 |
| Dynasilan® VTMO | Silane | 1 | 1 | 1 | 1 |
| Dynasilan® DAMO | Silane | 0.8 | 0.8 | 0.8 | 0.8 |
| Metatyn® KAT 740 | Tin salt | 0.7 | 0.7 | 0.7 | 0.7 |
| Total | | 96.2 | 100.0 | 100.0 | 100.0 |

*in the plasticizer (25% by weight of polyamide in 75% by weight of plasticizer).

Example 1 (Comparative)

Sealant without Rheological Additive

Dispersing is carried out at 2600 revolutions/min (8.8 m·s$^{-1}$) for 1 hours adiabatically under ambient conditions.

Example 2 (Comparative)

Sealant with a Crayvallac® SL Powder Additive

The dispersion is heated at 80° C. for 2 hours at 2600 revolutions/min in order to activate the powder additive having a maximum particle size of 15 μm.

At the end of the activation, after two hours, the speed of the Molteni is lowered to 1500 revolutions/min (5.1 m·s$^{-1}$) and the mixture is cooled by circulation of cold water in order to reach a temperature of less than 50° C.

Examples 3 and 4 (Invention)

Sealant with a Preactivated Paste Respectively in DIUP and in PPG 2000 (Preactivated Pastes Described Above in § III a) and b))

Dispersion is carried out at 2600 revolutions/min for 1 hour without heating. The addition of [N-(2-aminoethyl)-3-aminopropyl]trimethoxysilane (Dynasylan® DAMO) and of vinyltrimethoxysilane (Dynasylan® VTMO) is carried out at a temperature of less than 50° C. in order to prevent them from evaporating. When the temperature is less than 50° C., the adhesion promoter Dynasylan® DAMO and the dehydrating agent Dynasylan® VTMO are added and mixed under vacuum and with gentle stirring at 1000 revolutions/min for 15 min.

The catalyst is subsequently added and mixed under vacuum at 1000 revolutions/min for 10 min.

The sealant is subsequently placed in cartridges and then left to stand for at least 24 hours in a climate-controlled chamber at 23° C.

Results:

TABLE 5

| Consistency | |
| --- | --- |
| Displacement (penetration) of the needle into the preactivated paste based on DIUP (mm) | Displacement (penetration) of the needle into the preactivated paste based on PPG 2000 (mm) |
| 2.00 | 3.11 |

The invention claimed is:

1. A rheological additive in the form of a preactivated paste, wherein it consists of:
    A) at least one fatty acid diamide in a powder form, said powder optionally comprising in addition to said diamide, hydrogenated castor oil, the weight of said fatty acid diamide varying from 10 to 40%, with respect to the mixture A)+B) and said fatty acid diamide being obtained by polycondensation between at least one $C_2$ to $C_{12}$ primary diamine and at least one monocarboxylic acid with a chain length of $C_3$ to $C_{22}$, the reaction product optionally being diluted in hydrogenated castor oil to a level from 10 to 100% by weight based on the diamide +hydrogenated castor oil total weight; and
    B) at least one organic plasticizer, said plasticizer being liquid at room temperature and being a polar organic plasticizer bearing at least one of an ether group, ester group, epoxy group or a combination thereof;
    wherein the dynamic elastic modulus G' of said rheological additive in the form of a preactivated paste, measured on the mixture A)+B), at a temperature of 23° C. and under a frequency of 1 Hz, is greater than or equal to $10^4$ Pa, and the maximum penetration value of the final preactivated paste is less than 15 mm, measured according to standard ASTM D 217.

2. The additive as claimed in claim 1, wherein said plasticizer bears at least one ether group selected from the group consisting of polyethers which are homopolymers, copolymers of ethylene oxide, copolymers of propylene oxide, a blend of said polyethers, their derivatives or a combination thereof; said derivatives comprising said polyethers blocked at a chain end by a $C_1$ to $C_4$ alkoxy group or by a $C_2$ to $C_4$ ester group, said polyethers having a weight-average molecular weight Mw ranging from 150 to 6000.

3. The additive as claimed in claim 1, wherein said plasticizer bears at least one ester group and is selected from the group consisting of monoesters and polyesters obtained from $C_4$ to $C_{21}$ alcohols, which alcohols are optionally alkoxylated, and from mono- or polyacids with a functionality ranging from 1 to 4 selected from:
    organic acids selected from the group consisting of aromatic acids having a chain length ranging from $C_6$ to $C_{10}$ and aliphatic acids having a chain length ranging from $C_4$ to $C_{18}$, or
    inorganic acids.

4. The additive as claimed in claim 1, wherein said plasticizer is present in the absence of any other compound selected from the group consisting of alcohols with a molecular weight Mw <150 or polar aprotic solvents selected from the group consisting of: N-methylpyrrolidone, N-ethylpyrrolidone, N-butylpyrrolidone, acetonitrile, N,N-dimethyl forma-

TABLE 6

| Example | Rheological additive | Manufacturing time (min) | Appearance of the sealant | Extrudability (g/min) | Viscosities (mPa · s) | | | Thixotropic index |
| --- | --- | --- | --- | --- | --- | --- | --- | --- |
| | | | | | 1 rpm | 5 rpm | 10 rpm | |
| Ex. 1 | Additive-free | 90 | good | 1430 | 80 000 | 40 000 | 28 000 | 2.9 |
| Ex. 2 | Crayvallac ® SL | 260 | good | 790 | 1 130 000 | 412 000 | 259 000 | 4.4 |
| Ex. 3 | Paste in DIUP | 90 | good | 595 | 1 460 000 | 544 000 | 348 000 | 4.2 |
| Ex. 4 | Paste in PPG 2000 | 100 | good | 581 | 1 410 000 | 548 000 | 353 000 | 4.0 | mide, N,N-dimethylacetamide, dimethyl sulfoxide, N,N,N', N'-tetramethylurea, hexamethylphosphoramide, hexamethyl-phosphorous triamide and propylene carbonate.

5. The additive as claimed in claim 2, wherein said plasticizer is selected from polyethers which are homopolymers of propylene oxide with a weight-average molecular weight Mw ranging from 1000 to 3000, and derivatives thereof.

6. The additive as claimed in claim 3, wherein said plasticizer comprises at least one $C_6$ to $C_{10}$ aromatic acid ester group selected from the group consisting of mono- and/or dialkyl phthalates, said dialkyl alkyls being identical or different and chosen from $C_7$ to $C_{18}$ alkyls.

7. The additive as claimed in claim 6, wherein said plasticizer is a di-iso-undecyl phthalate.

8. The additive as claimed in claim 3, wherein said plasticizer is a sulfonic ester selected from $C_{10}$ to $C_{21}$ alkyl sulfonates.

9. The additive as claimed in claim 1, produced by a process comprising the following steps:
   i) progressive dispersing of said diamide in the powder form, in said plasticizer until a homogeneous dispersion is obtained, at room temperature controlled by regulation of the temperature,
   ii) maintaining the homogeneous dispersion obtained during step i) at least one isotherm with a corresponding temperature ranging from 50 to 120° C., for a period of 1 to 100 hours.

10. An organic binder composition, pigment concentrate composition or fillers composition, wherein the composition comprises, in addition to said binder, pigment or filler, at least one additive as defined in claim 1.

11. The composition as claimed in claim 10, wherein said additive is present at a weight ratio varying from 1 to 40%, with respect to the total weight of said composition.

12. The composition as claimed in claim 10, wherein said diamide is present as dry active material at a content by weight varying from 0.1 to 16%, with respect to the total weight of said composition.

13. The organic binder composition as claimed in claim 10, wherein the composition is a coating, sealant, glue, adhesive, sealer, molding or cosmetic composition.

14. The organic binder composition as claimed in claim 13, wherein the composition is a one-component or a two-component crosslinkable composition and said organic binder is selected from the group consisting of at least one epoxy/amine reactive system, an unsaturated polyester, a vinyl ester, an epoxidized resin, a reactive silicone resin, an alkyd grafted by a polyester or a polyamide, an alkyd modified by diurea/diurethane or an ungrafted alkyd, a polyurethane or a silicone, a crosslinkable two-component polyurethane, a polysiloxane, a polysulfide polymer, a reactive acrylic polymer, a (meth)acrylate multifunctional oligomer, an acrylated acrylic oligomer, an allylic multifunctional oligomer, a butyl rubber, polychloroprene or SBR type elastomer, a silylated prepolymer or polymer, and a silylated polyether-urethane with an —OH or —$CO_2H$ functional group.

15. The organic binder composition as claimed in claim 13, wherein the composition is a sealant, glue, adhesive or sealer composition which is self-crosslinkable and based on a polyether-silane or on a polyurethane-silane composition.

16. The organic binder composition as claimed in claim 13, wherein the composition is a coating composition for protection, decoration, surface treatment or combination thereof, of a substrate, said coating composition being a composition selected from the group consisting of paints, varnishes, gel coats, inks and plastisols based on PVC.

17. A coating selected from the group consisting of paints, varnishes, inks, gel coats, plastisols based on PVC, a sealant, a glue, an adhesive, a sealer, a composite, a molded compound, an SMC/BMC laminate, and a cosmetic product, which comprises at least one additive as defined in claim 1.

* * * * *